United States Patent [19]

Tamura et al.

[11] Patent Number: 5,256,701
[45] Date of Patent: Oct. 26, 1993

[54] DISINFECTANT COMPOSITION

[75] Inventors: Zenzo Tamura, 17-11, Sanno 2 chome, Ota-ku, Tokyo; Kuniko Shoji, Kanagawa; Chieko Azegami, Kanagawa; Takao Kunisada, Kanagawa; Kaoru Hosoi, Kanagawa; Kiwa Suzuki, Tokyo; Shikifumi Kitazawa, Chiba, all of Japan

[73] Assignees: Zenzo Tamura; Meiji Seika Kaisha Ltd., both of Tokyo, Japan

[21] Appl. No.: 794,248

[22] Filed: Nov. 19, 1991

[30] Foreign Application Priority Data

Nov. 19, 1990 [JP] Japan ................................. 2-311400

[51] Int. Cl.$^5$ ..................... A01N 25/00; A01N 59/12
[52] U.S. Cl. ........................... 514/781; 424/667; 424/669; 424/670; 424/671; 424/672; 424/78.37
[58] Field of Search ............... 424/488, 667, 669, 670, 424/671, 672; 514/57, 781

[56] References Cited

U.S. PATENT DOCUMENTS 4,364,929 12/1982 Sasmor et al. ................. 424/667
4,996,048 2/1991 Bhagwat et al. ............... 514/967

FOREIGN PATENT DOCUMENTS 0196813 10/1986 European Pat. Off. .
612090 7/1975 Switzerland .
824215 11/1959 United Kingdom .

OTHER PUBLICATIONS

European Search Report (1992).
Remington's Pharmaceutical Sciences, 15th edition, Easton (Pa.), Mack Publishing Company, 1975. pp. 391-392, 1092-1093, 1098 and 1244.
WPIL, File Supplier, Accession No. 82-35994E (18), Derwent Publications Ltd., London, GB; and JP-A-57050907 (Mitsubishi Rayon) Mar. 25, 1982.

*Primary Examiner*—Allen J. Robinson
*Assistant Examiner*—John D. Pak
*Attorney, Agent, or Firm*—Sughrue, Mion, Zinn, Macpeak & Seas

[57] ABSTRACT

A disinfectant composition comprising an aqueous solution or an alcoholic aqueous solution in a concentration of 83 v/v % or less which contains hydroxypropyl cellulose in a concentration of from 0.5 to 10 w/v %, iodine in a concentration of from 0.01 to 1.0 w/v %, and an iodide in a concentration of not more than 0.5 w/v %. The composition has reduced skin irritation while exhibiting sufficient bactericidal and viricidal activity.

3 Claims, 1 Drawing Sheet

DISINFECTANT COMPOSITION

FILED OF THE INVENTION

This invention relates to a disinfectant composition and, more particularly, to an iodine-based disinfectant composition.

BACKGROUND OF THE INVENTION

Various disinfectant compositions have hitherto been used for disinfection of the site of operation, wounded sites, burnt skin, and infected skin.

Disinfectants containing iodine as an active ingredient exhibit bactericidal activity on various bacteria. Such iodine-based disinfectants typically include iodine tincture and povidone-iodine solution.

Since iodine is sparingly soluble in water, iodine tincture is prepared by adding to iodine potassium iodide and ethanol to dissolve. This preparation strongly irritates the skin. If iodine tincture is diluted with water in order to allay the skin irritation, part of iodine is precipitated to lessen the bactericidal activity.

Povidone-iodine solution is an aqueous solution of a polyvinyl pyrrolidone-iodine complex. Disadvantages of povidone-iodine solution lie in its relative expensiveness and strong complex-forming ability of polyvinyl pyrrolidone which sometimes requires concentration adjustment for manifestation of sufficient bactericidal effects.

Disinfectants are required to exert potent bactericidal activity on a broad range of bacteria and to have skin irritation minimized. It is desirable that disinfectants also have viricidal activity in addition to these requirements.

While it has been reported that the bactericidal and viricidal activities essentially exhibited by iodine-based disinfectants are attributed to free iodine of unbound form, a higher free iodine concentration is known to induce stronger irritation to the skin. It is important, as is implied by this fact, to preliminarily grasp a proper range of free iodine concentration in which bactericidal and viricidal activities can be manifested while suppressing skin irritation and to establish a method for easily and appropriately setting the free iodine concentration within such a proper range.

It is also important for an iodine-based disinfectant composition to contain an adequate amount of iodine in a bound form, e.g., a complex form, so as to make up for the loss of free iodine resulting from consumption during disinfection. Further, the amount each of free iodine and bound iodine and the free iodine to bound iodine ratio should be determined taking the end use of the disinfectant composition into consideration. Thus, it is also of importance that these factors may be arbitrarily adjusted.

SUMMARY OF THE INVENTION

Accordingly, an object of the present invention is to provide an iodine-based disinfectant composition which is less irritative to the skin, which has high bactericidal and viricidal activity, which is relatively cheap, and which meets various purposes.

The inventors have conducted extensive investigations and, as a result, have found that a proper concentration of free iodine of unbound form at which irritation to the skin is minimized while exhibiting sufficient bactericidal activity and viricidal activity ranges from 1 to 100 ppm, and preferably from 5 to 50 ppm.

The inventors have further studied complex-forming ability of various water-soluble high polymers with iodine by utilizing spectrometry, etc. As a result, they have also found that (a) hydroxypropyl cellulose is suitable as a water-soluble high polymer capable of forming a complex with iodine from the standpoint of reduced skin irritation, (b) hydroxypropyl cellulose is capable of forming a complex with iodine and a triiodide, and (c) the concentration of iodine either in free or bound form can properly be adjusted by altering the concentrations of hydroxypropyl cellulose, iodine, and a triiodide and their ratio.

That is, the present invention relates to a disinfectant composition comprising an aqueous solution or an alcoholic aqueous solution in a concentration of 83 v/v % or less which contains hydroxypropyl cellulose in a concentration of from 0.5 to 10 w/v %, iodine in a concentration of from 0.01 to 1.0 w/v %, and an iodide in a concentration of not more than 0.5 w/v %.

DETAILED DESCRIPTION OF THE INVENTION

Figure 2:
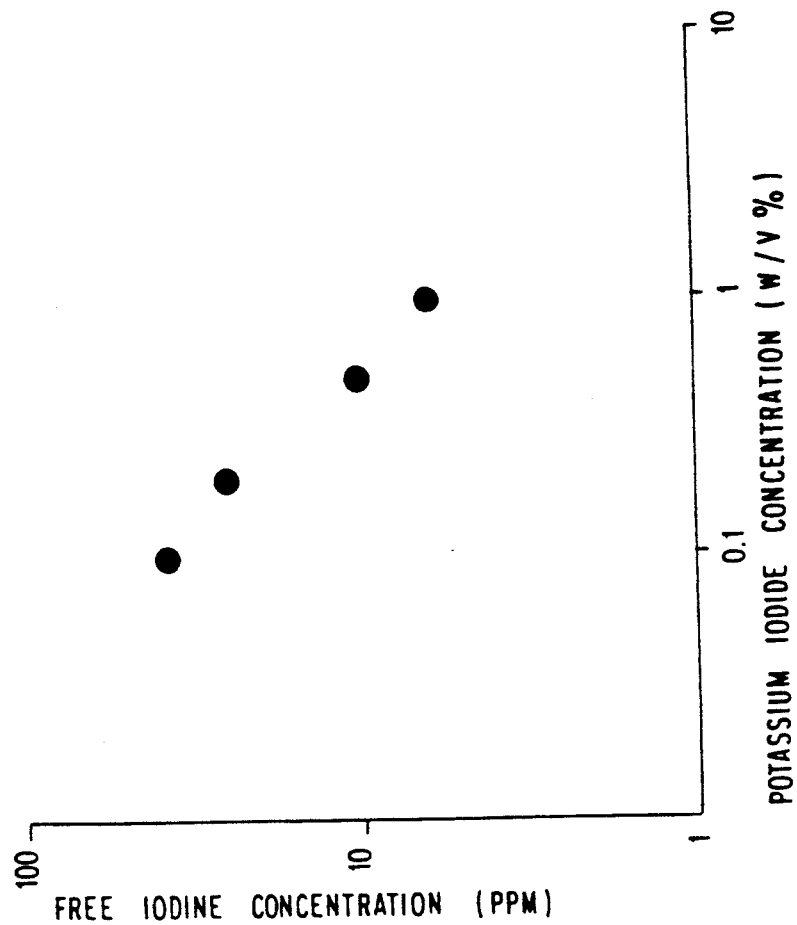
FIG. 2 shows the plot of free iodine concentration vs. varied amount of potassium iodide added.

Any of commercially available hydroxypropyl cellulose species having various viscosity characteristics according to molecular weight or degree of substitution of a hydroxypropoxy group can be used in the present invention. If desired, two or more species different in quality or characteristics may be used in combination.

The iodide which can be used in the present invention is not particularly limited to specific compounds, and any iodides are employable as long as they are of low toxicity. Suitable examples are potassium iodide, sodium iodide, and hydrogen iodide. These iodides may be used either individually or in combination of two or more thereof.

The above-described hydroxypropyl cellulose and iodide are used for proper adjustment of the concentration or amount each of free iodine and bound iodine in agreement with the end use of the disinfectant composition, and their amounts are appropriately selected to that effect.

In order to adjust the free iodine concentration within its proper range as recited above, i.e., of from 1 to 100 ppm, hydroxypropyl cellulose, iodine and iodide are used in a concentration of from 0.5 to 10 w/v %, from 0.01 to 1.0 w/v % and not more than 0.5 w/v %, respectively.

Solvents to be used for preparation of the disinfectant composition of the present invention include water and an alcoholic aqueous solution in a concentration of not more than 83 v/v %, which is the highest concentration of commonly employed alcohols as a disinfectant. Usable as an aqueous solvent are various buffer solutions such as a citrate buffer and a phosphate buffer in order to appropriately adjust the pH value of the disinfectant composition. The pH value suitably ranges from 2 to 7 in view of irritation of skin and stability of iodine. The viscosity of the composition is properly adjusted depending on the end of the use.

The disinfectant composition according to the present invention is useful as not only disinfectants for external use but gargles, eye drops, ear drops, nose drops, shampoos, etc.

The disinfectant composition may further contain additives such as surfactants, buffers, flavors, viscosity-increasing agents, humidifiers and perfumes. The additives are not particularly restricted as long as they have low reactivity with iodine.

The disinfectant compostion can be applied to sites of skin, tissue or instruments to be disinfected. The dosage and the mode of application varies depending on the application sites, symptom and so on.

In the disinfectant composition according to the present invention, hydroxypropyl cellulose brings about a proper viscosity and also forms a complex with iodine to reduce a free iodine content. By these actions combined, skin irritation is alleviated. Further, the disinfectant composition of the invention is excellent in bactericidal and viricidal activity and can be prepared at a lower cost than povidone-iodine solution.

Since the amounts of hydroxypropyl cellulose and the iodide in the composition may be altered in a relatively broad range, the concentration of free iodine and bound iodine in the final product can be adequately set according to the end use of the product. Therefore, the composition has a broad range of application as not only disinfectants for external use but also gargles, eye drops, nose drops, shampoos, etc.

The present invention is now illustrated in greater detail with reference to Examples, but it should be understood that the present invention is not deemed to be limited thereto. In the description hereinafter given, all the percents are by weight per volume unless otherwise indicated.

Abbreviations HPC-SL, HPC-L, HPC-M, and HPC-H used in Examples designate hydroxypropyl cellulose species having a viscosity of 3.0 to 5.9 cps, 6.0 to 10.0 cps, 150 to 400 cps, and 1000 to 4000 cps, respectively, in a 2% aqueous solution.

EXAMPLE 1

Figure 1:
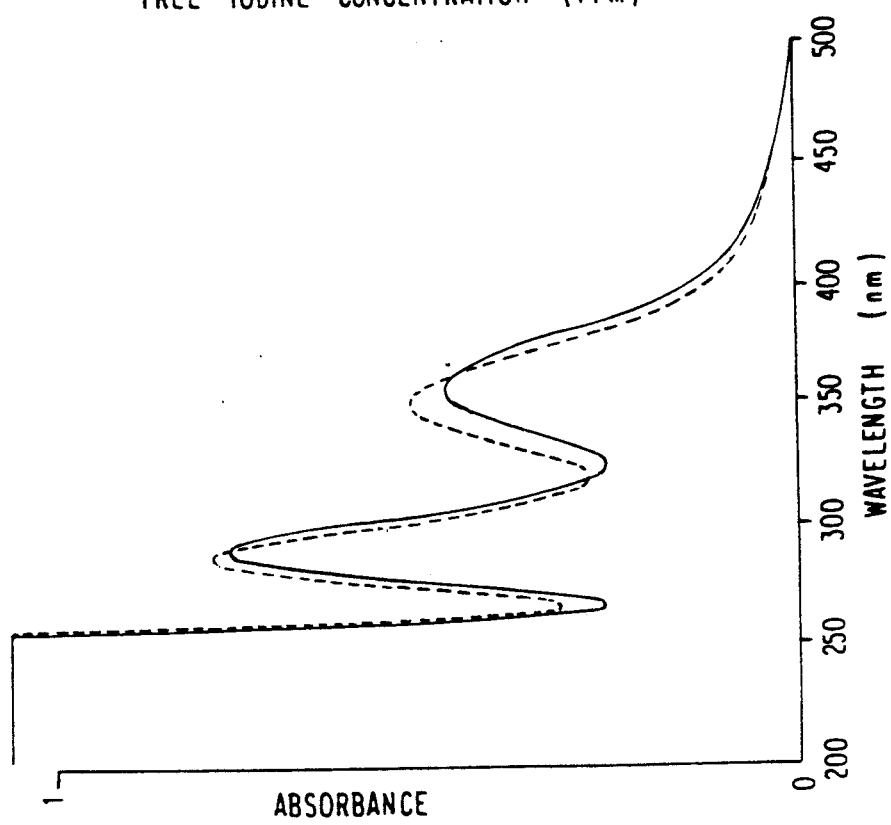
FIG. 1 shows the visible to ultraviolet absorption spectrum of an aqueous solution containing iodine and potassium iodide with (solid line) or without hydroxypropyl cellulose (dotted line).

An aqueous solution containing $1\times 10^{-4}$ M of iodine and $5\times 10^{-5}$ M of potassium iodide and an aqueous solution additionally containing 1% of HPC-M were prepared, and the visible to ultraviolet absorption spectrum of each solution was determined. The results obtained are shown in FIG. 1. It is seen that the absorption peaks of a triiodide at wavelengths of about 280 nm and 350 nm were shifted to the longer wavelength side by addition of HPC-M, indicating formation of a complex of HPC-M and the triiodide.

EXAMPLE 2

To 100 ml of a saturated iodine aqueous solution was added 4.9 g of iodic acid to oxidize an iodide and a triiodide which might be present there. To the resulting pure iodine aqueous solution was added HPC-M to a concentration of 1%, and the solution was transferred to a container with its top open. The absorbance of the solution at a wavelength of around 460 nm, which is the absorption maximum of iodine, was measured with time. For control, the absorbance of the pure iodine aqueous solution containing no HPC-M was measured in the same manner.

The results obtained are shown in Table 1 below. It can be seen that HPC-M and iodine formed a complex and suppressed evaporation of iodine.

TABLE 1

| Sample | Absorbance (Ratio to Initial) | | |
| --- | --- | --- | --- |
| | Initial | After 4 Hrs | After 10 Hrs |
| Test Sample | 0.712 (100%) | 0.401 (56%) | 0.175 (25%) |
| Control | 0.665 (100%) | 0.126 (19%) | 0.011 (2%) |

EXAMPLE 3

To 0.5 g of HPC-SL, HPC-L, HPC-M, or HPC-H was added an aqueous solution containing 0.05% iodine and 0.05% potassium iodide to make 100 ml. Each of the resulting solutions was preserved in a closed container overnight.

Starch paper was inserted into the space of the container for 10 seconds, and the tone of the starch paper thus colored with iodine vapors was visually observed. The results obtained are shown in Table 2 below. From the results in the table, it was confirmed that hydroxypropyl cellulose (HPC) formed a complex with iodine to suppress evaporation of iodine and that the degree of the complex formation or the suppression of iodine evaporation does not depend on the kind of HPC. In other words, any HPC of various quality and characteristics proved usable for formation of a complex with iodine.

TABLE 2

| HPC | Tone of Starch Paper |
| --- | --- |
| None | Bluish purple |
| HPC-H | Pale bluish purple |
| HPC-M | Pale bluish purple |
| HPC-L | Pale bluish purple |
| HPC-SL | Pale bluish purple |

EXAMPLE 4

In 100 ml of a saturated iodine aqueous solution was dissolved 0.3 g of HPC-M, and potassium iodide was added to the solution in an amount varying from 0.1 g to 1.0 g. The free iodine concentration of each solution was obtained from the rate of permeation through a polyethylene membrane. The results obtained are shown in FIG. 2.

EXAMPLE 5

A saturated iodine aqueous solution was added to 1, 5, 10, or 20 g of HPC-SL to make 100 ml. After the solution was preserved in a closed container overnight, the container was opened, and the appearance of the solution was visually observed, and the viscosity of the solution was measured. The results obtained are shown in Table 3 below.

TABLE 3

| Amount of HPC-SL Added (g) | Viscosity (cps) | Appearance |
| --- | --- | --- |
| 1 | 5 | Brown liquid |
| 5 | 24 | Brown liquid |
| 10 | 155 | Slightly viscous, pale brown liquid |
| 20 | 1788 | Viscous colorless liquid |

EXAMPLE 6

Two grams of HPC-SL and 0.1, 0.5, or 1.0 g of HPC-H were weighed and mixed. An aqueous solution containing 0.05% of iodine and 0.5% potassium iodide was added to the mixed HPC to make 100 ml. After preserving each solution in a closed container overnight, the viscosity was measured. The results obtained are shown in Table 4 below.

TABLE 4

| Amount of HPC-H Added (g) | Viscosity (cps) |
|---|---|
| 0 | 8 |
| 0.1 | 12 |
| 0.5 | 73 |
| 1.0 | 395 |

EXAMPLE 7

Preparations 1 to 5 were prepared in the following manner.

Preparation 1: Disinfectant for External Use

Five grams of HPC-L were dissolved in 50 ml of a 10 mM citric acid buffer (pH 5.5) containing 0.2% sodium dioctylsuccinate, and 50 ml of an iodine-saturated 1% potassium iodide aqueous solution was added thereto to prepare a disinfectant for external use.

Preparation 2: Eye Drops

In 50 ml of a 5 mM boric acid buffer (pH 5.5) was dissolved 1.0 g of HPC-M, and 50 ml of an aqueous solution containing 0.05% iodine and 0.05% potassium iodide was added thereto to prepare eye drops.

Preparation 3: Bactericidal Detergent for Hands

In 90 ml of a 2 mM citric acid buffer (pH 5.5) were dissolved 1 g of ammonium nonylphenoxypolyethylene ethanesulfate and 0.03 g of potassium iodide. To the solution was added 0.1 g of iodine powder and thoroughly stirred to dissolve. To the resulting solution was added 1.5 g of HPC-M and mixed uniformly to prepare a bactericidal detergent for hands.

Preparation 4: Rub Type Disinfectant for Hands

In 100 ml of 83 v/v % ethanol were dissolved 0.05 g of iodine, 0.01 g of potassium iodide, and 0.5 g of glycerin to prepare a rub type disinfectant for hands.

Preparation 5: Gargle

One gram of HPC-M was uniformly mixed with 50 ml of a 2 mM citric acid buffer (pH 4.5) containing 0.1 g of potassium iodide, and 30 ml of 95 v/v % ethanol containing 1 g of iodine was added thereto. In the resulting solution were dissolved 0.2 g of saccharin sodium, 0.1 g of l-menthol, and 0.15 g of eucalyptus oil to prepare a gargle.

The resulting gargle is a stock liquid which is about 10 fold diluted with water on use.

Bactericidal activity of each preparation obtained as described above was examined in accordance with a modified test method of phenol index using *Staphylococcus aureaus* as a test microorganism.

Each preparation required a working time of within 30 seconds for disinfection, proving to have excellent bactericidal activity.

EXAMPLE 8

To 2 g of HPC-M was added an aqueous solution containing 0.1% of iodine and 0.2% of potassium iodide to make 100 ml. The resulting solution was applied to the shaved back of a rabbit five times a day for consecutive 7 days, and the condition of the applied skin was observed and evaluated according to Draise's standard. The results obtained are shown in Table 5 below. It can be seen that the solution caused substantially no skin irritation.

TABLE 5

| Day of Observation | Rash and Crust | Edema |
|---|---|---|
| During the period of application: | | |
| 1st Day | 0 | 0 |
| 3rd Day | 0 | 0 |
| 5th Day | 0.17 + 0.41 | 0 |
| 7th Day | 0.50 + 0.55 | 0 |
| During the period of recovery: | | |
| 9th Day | 0.50 + 0.55 | 0 |
| 11th Day | 0 | 0 |
| 13th Day | 0 | 0 |
| 15th Day | 0 | 0 |

While the invention has been described in detail and with reference to specific examples thereof, it will be apparent to one skilled in the art that various changes and modifications can be made therein without departing from the spirit and scope thereof.

What is claimed is:

1. An aqueous disinfectant composition consisting essentially of 0.5–10 w/v % of hydroxypropyl cellulose, 0.01–1.0 w/v % of iodine, 0–0.5 w/v % of an iodide, 0–83 v/v % of an alcohol and water in an amount to make up the balance.

2. A disinfectant composition as claimed in claim 1, wherein said iodide is selected from potassium iodide, sodium iodide and hydrogen iodide.

3. A method of disinfecting skin, tissue, or instruments in need of disinfection, comprising applying to said skin, tissue, or instruments in need of disinfection, an effective disinfecting amount of an aqueous composition consisting essentially of 0.5–10 w/v % of hydroxypropyl cellulose, 0.01–1.0 w/v % of iodine, 0–0.5 w/v % of an iodide, 0–83 v/v % of an alcohol and water in an amount to make up the balance.

* * * * *